(12) United States Patent
Code et al.

(10) Patent No.: US 10,046,078 B2
(45) Date of Patent: Aug. 14, 2018

(54) LIQUID IODINE MIST TREATMENT OF SEPARATED ODOR-EMITTING DRY WASTE WITHIN A WASTE MANAGEMENT FACILITY

(71) Applicants: Kenneth R. Code, Alberta (CA); Joseph Provenzano, Huntington Beach, CA (US)

(72) Inventors: Kenneth R. Code, Alberta (CA); Joseph Provenzano, Huntington Beach, CA (US)

( * ) Notice: Subject to any disclaimer, the term of this patent is extended or adjusted under 35 U.S.C. 154(b) by 0 days.

(21) Appl. No.: 15/186,482

(22) Filed: Jun. 19, 2016

(65) Prior Publication Data

US 2017/0043049 A1 Feb. 16, 2017

Related U.S. Application Data

(63) Continuation-in-part of application No. 14/171,703, filed on Feb. 3, 2014, now abandoned, which is a continuation-in-part of application No. 13/843,615, filed on Mar. 15, 2013, now Pat. No. 8,846,067, and a continuation-in-part of application No. 13/308,105, filed on Nov. 30, 2011, now Pat. No. 8,642,057, which is a continuation-in-part of application No. 12/009,585, filed on Jan. 18, 2008, now abandoned.

(51) Int. Cl.
*A61L 11/00* (2006.01)
*A01N 59/12* (2006.01)
*C02F 9/00* (2006.01)

(52) U.S. Cl.
CPC .............. *A61L 11/00* (2013.01); *A01N 59/12* (2013.01); *C02F 2303/02* (2013.01)

(58) Field of Classification Search
CPC ......... A61L 11/00; A01N 59/12; A01N 25/02; A01N 25/08; A01N 25/22; A01N 59/20; A01N 2300/00; B01D 21/02; B01D 27/08; B01D 29/21; B01D 35/06; B01D 2201/50
USPC .................. 204/228.3, 228.6, 230.2, 237
See application file for complete search history.

(56) References Cited

U.S. PATENT DOCUMENTS 4,948,787 A * 8/1990 Chen .................. A01N 57/02
514/141
5,984,993 A * 11/1999 Mainz .................. A61L 9/01
210/758

(Continued)

*Primary Examiner* — Hayden Brewster
(74) *Attorney, Agent, or Firm* — Mark A. Litman & Assoc. P.A.

(57) ABSTRACT

A system for applying a novel odor abating solution to an odor-emitting surface includes a storage compartment comprising a solution of iodine having a concentration of at least 0.0005% by total weight of the solution of $I_2$; a misting system having mist nozzles that are supported over the odor-emitting surface, creating an aerial environment between the odor-emitting surface and the mist nozzles; misting nozzles configured to spray droplets of the solution into the aerial environment over the odor-emitting surface so that, in absence of any air movement exceeding 1 kilometer/hour, at least 75% of the droplets are suspended in the aerial environment over the odor-emitting surface for at least 10 seconds, allowing at least 1% by weight of the $I_2$ in the solution to react with emitted odor before the 75% of the droplets are deposited on the odor-emitting surface. The odor-emitting surface may be within a waste transfer station.

14 Claims, 7 Drawing Sheets

(56) References Cited

U.S. PATENT DOCUMENTS

Figure 3:
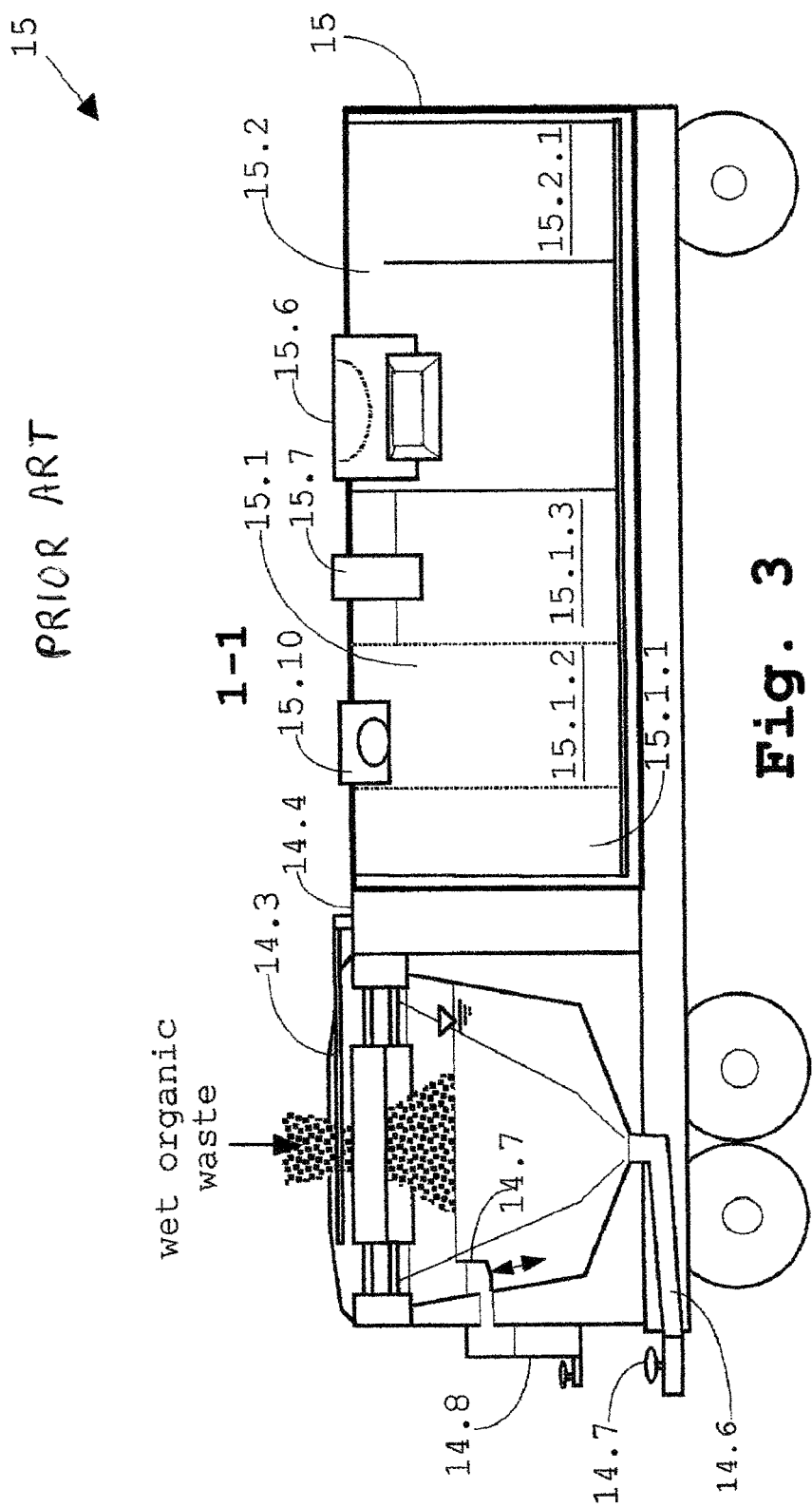

2007/0142260 A1* 6/2007 Tasz ................ A01N 25/06
510/384
2012/0087965 A1* 4/2012 Code ................ A01N 59/12
424/408

* cited by examiner

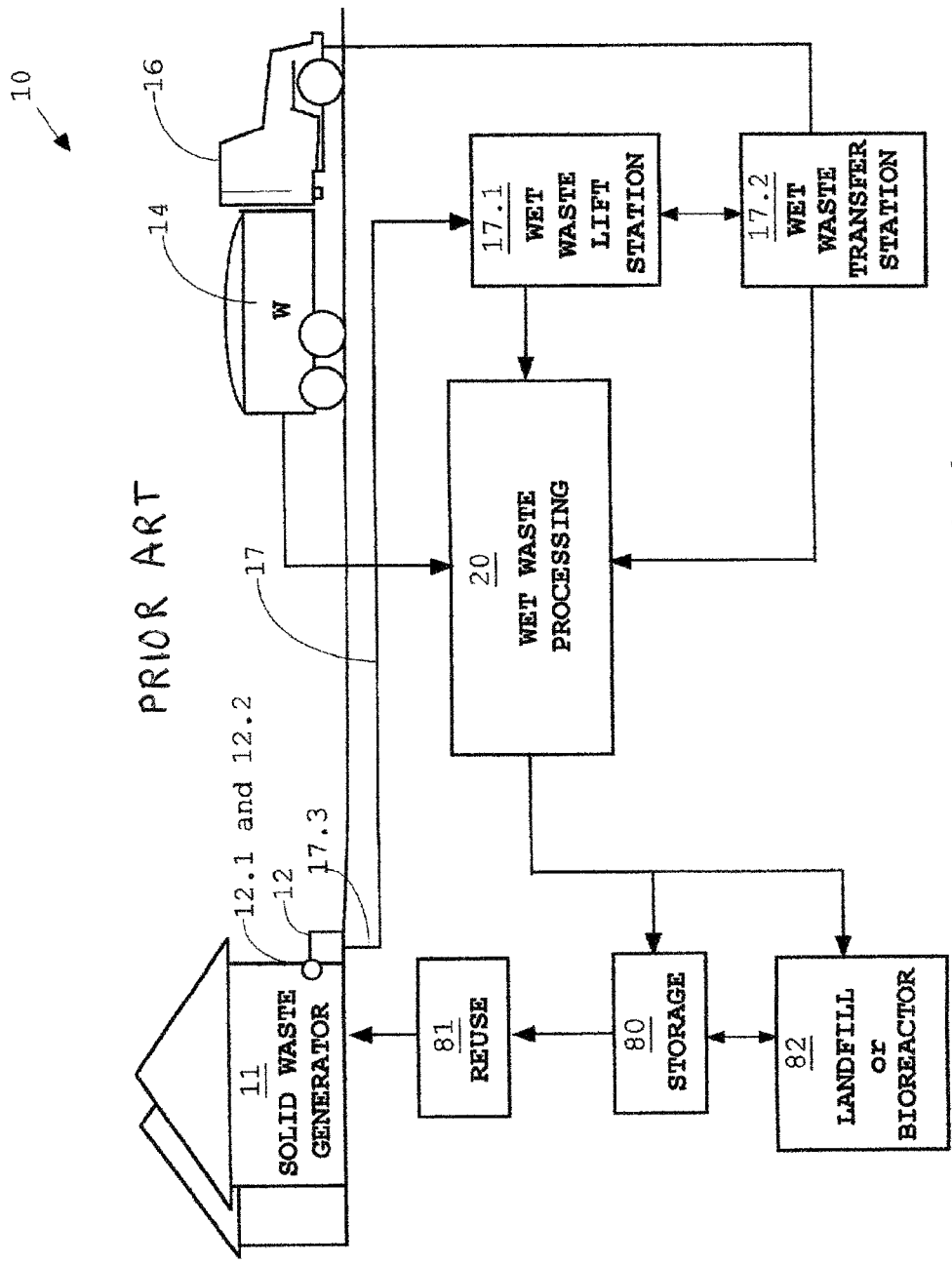
Fig. 1.1

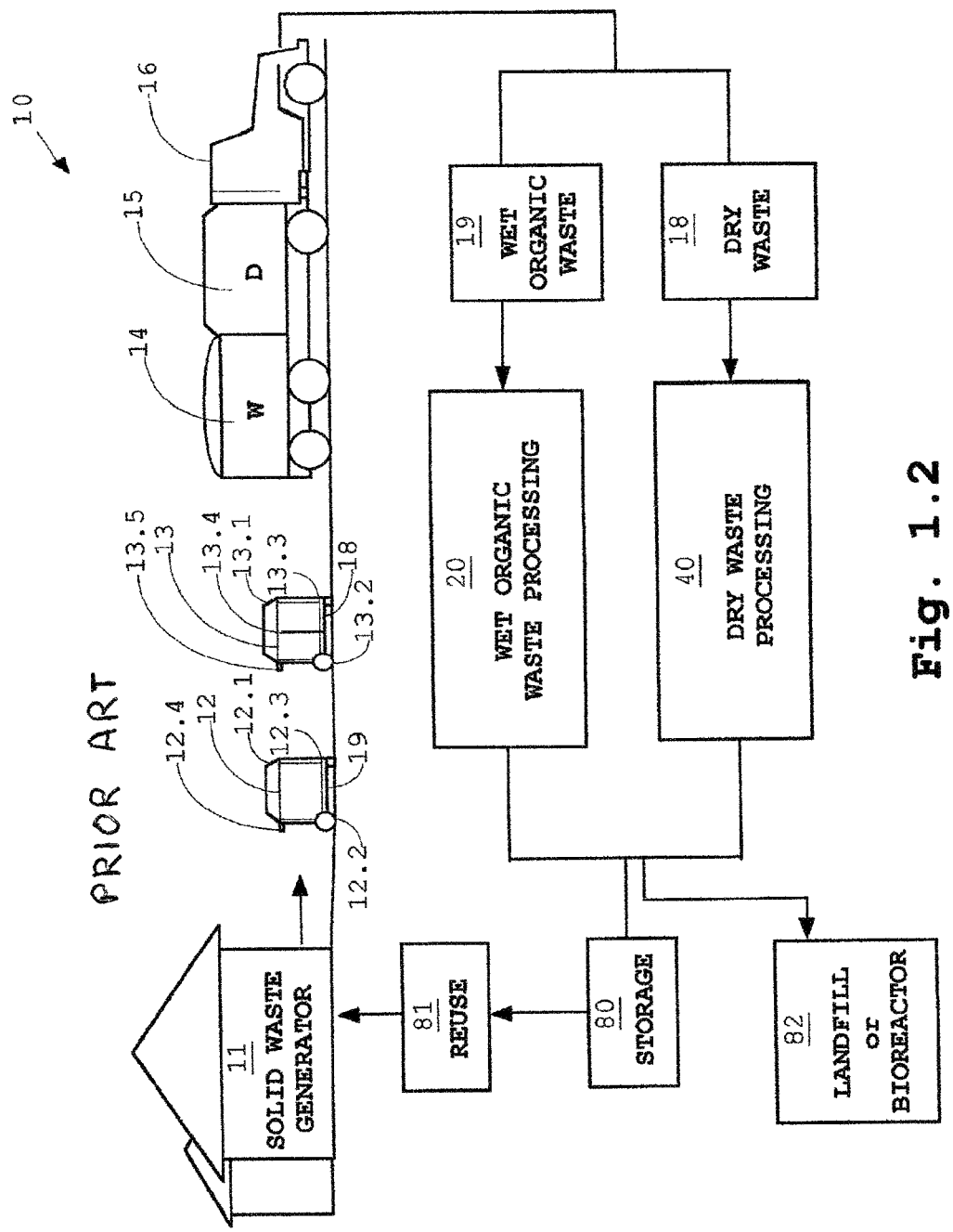
Fig. 1.2

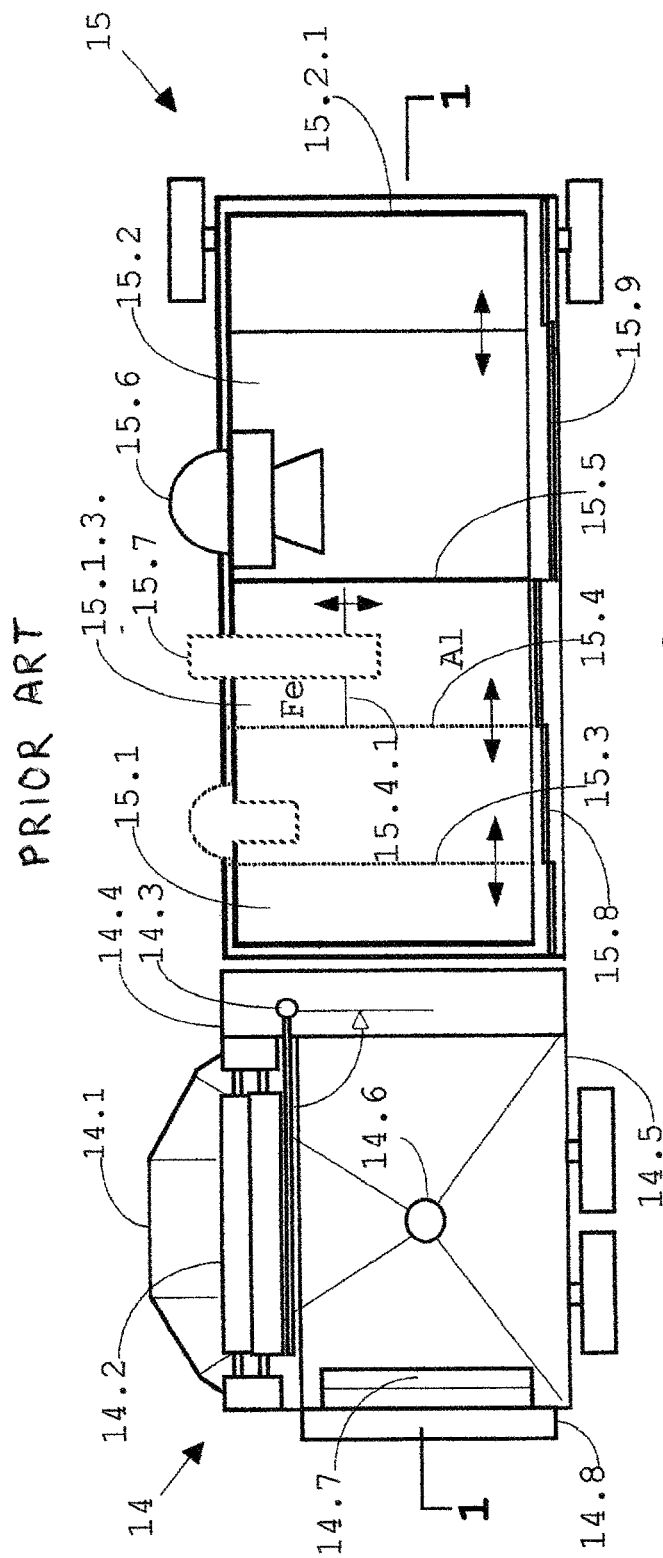

LIQUID IODINE MIST TREATMENT OF SEPARATED ODOR-EMITTING DRY WASTE WITHIN A WASTE MANAGEMENT FACILITY

RELATED APPLICATIONS DATA SECTION

This application claims priority under 35 U.S.C. 120 through the following priority chain starting with U.S. Ser. No. 14/171,703 filed 3 Feb. 2014 as continuation-in-part of U.S. Ser. No. 13/843,615 filed Mar. 15, 2013 (Antimicrobial solutions and methods), now U.S. Pat. No. 8,846,067, which in turn claims priority from U.S. Ser. No. 13/308,105, filed 30 Nov. 2011 (Antimicrobial and antiodor solutions and delivery systems), which in turn claims priority as a continuation-in-part application from U.S. Ser. No. 13/116,775, filed 26 May 2011 (Moderation of oil extraction waste environments), which in turn claims priority from U.S. Ser. No. 12/009,585, filed Jan. 18, 2008 (Systems and methods for cleaning liquid carriers related applications data), now U.S. Pat. No. 8,226,964.

BACKGROUND OF THE INVENTION

1. Field of the Invention

The present invention relates to the field of odor abatement, and especially odor abatement in the trash, garbage and recycling venue.

2. Background of the Art

Transfer Stations generally refer to a solid waste management facility including a recyclables handling and recovery facility, but not generally including used oil facility, or a construction and demolition debris processing facility, where solid waste is received for the purpose of subsequent transfer to another solid waste management facility for further processing, treating, transfer or disposal. Transfer of solid waste from vehicle to vehicle for the purpose of consolidating loads, as part of the initial collection process, is not usually considered a transfer station provided the transfer activity occurs along the collection route where the point of transfer changes from day to day, but similar issues addressed by the present invention are also present there. Transfer of leak-proof, closed containers of solid waste from vehicle to vehicle, including truck to train, for the purpose of consolidating loads for shipment to an authorized disposal or treatment facility, is usually not considered a transfer station provided: the contents of each container remain in their closed container during the transfer between vehicles; storage remains incidental to transport at the location where the containers are consolidated; containers are acceptable to the department and maintained in a safe, nuisance-free (e.g., dust, odor, noise, etc.) manner; and, the transfer location is under the ownership or control of the transporter.

A waste transfer station is a light industrial facility where municipal solid waste is temporarily staged in the course of its eventual journey to the landfill or waste-to-energy facility. Typical activities at the waste transfer station involved the unloading of garbage trucks, pre-screening and removal of inappropriate items such as automobile batteries, compacting and then reloading onto larger vehicles, including trucks, trains and barges to their final destination. In urban areas, the location of waste transfer stations can be very controversial. Such facilities are typically fully enclosed.

The transfer station is a key component of cost-effective solid waste transportation. By transferring waste from local collection vehicles onto larger trailers or other transport modes such as barge and rail, the cost of transportation to distant disposal sites can be significantly reduced, freeing collection-specific vehicles and crews to devote their time to actual collection activities. A transfer station is a solid waste management facility where solid waste is received for the purpose of subsequent transfer to another solid waste management facility for further processing, treatment, transfer or disposal.

Provides fuel savings, reduction in road wear and less air pollution due to fewer vehicles being on the road Provides a trash and recyclable material drop-off location for citizens Reduces total traffic congestion in the community by transferring it onto larger vehicles Reduces total truck traffic and improves safety at the landfill or waste-to-energy facility Provides the opportunity to screen incoming trash for such purposes as removing hazardous waste or recovering recyclables Although waste transfer stations are a key component of modern waste management programs, the location of such stations can be a flashpoint for local concerns of citizens and typical management measures. This is particularly true where the transfer station is efficiently located to be near collection points, including residential and commercial areas.

A most important issue with many types of trash, especially organic material, is an odor problem. Odor problems are insufficiently addressed, even with attention to facility and doorway location, air venting systems, and a first in-first out system to ensure that garbage does not remain at the transfer station longer than necessary.

Many jurisdictions have extensive regulations and requirements for installation and location of transfer stations, focusing particularly on odor control.

This problem has been recognized in many jurisdictions and by many different types of industries. The most common forms of attempting merely odor abatement is the use of fragrances and odor vectors, which merely add more smell to cover up an underlying intolerable odor is overwhelmed by a second odor. The shortcomings of such a procedure are apparent, with the secondary odor, even if overwhelming the underlying odor, itself being an undesirable environment issue. Any single odor or combination of odors is undesirable in constant and large intensity.

Incineration of the underlying materials is not useful where materials are being transferred to different end-point locations, and incineration creates its own pollutant and odor issues.

Other commercial systems assert that particulate odor-causing materials can be encapsulated, that essential oils (another term for certain fragrances), filters, bacteria filter masses, enzyme treatments, ozone treatment and the like offer solutions to the problem, but there is still great dissatisfaction in the industries and in the communities surrounding the transfer stations with regard to odor abatement by these methods.

A preferred method of application of the treatment materials is by spraying, misting or atomizing of the treatment solutions around or onto the areas where odor is present. Examples of prior art systems and materials that have been used in the past and which can be used with the materials and processes of the present invention are identified below.

Published US Patent Application Document 20030003568 (Yilmaz) asserts that waste management by source eliminates a need for large landfills by separating waste into wet organic waste and dry waste and processing said waste for reuse prior to landfill application. Waste management by source integrates collection and transportation of waste with separation, treatment, processing, and recovery using a collection apparatus, one or a combination of hydrotransportation system and a transportation vehicle, a wet organic waste processing plant, and a dry waste processing facility for reuse. Since untreated organic waste is eliminated or significantly reduced from waste stream, present invention eliminates a need for daily cover and working front of landfills resulting in elimination of extensive leachate management systems and associated potential groundwater and air pollution problems.

Published US Patent Application Document 20140166693 (Williams) discloses an integrated material transfer and dispensing system for storing, transferring and dispensing materials, such as fluids and liquids, for example, liquid applied sound deadener (LASD). The system includes at least one vessel having a force transfer device. Each vessel may be removably enclosed in cabinet to form an automated station. Each vessel may be configured with a data logger, cleanout port, a sample valve at least one sight window and an access port for introducing a compound such as a biocide. Each vessel may be configured with instruments including sensors for measuring process variables, such as material volume, level, temperature, pressure and flow. The system may further include a metering device system and a robotic material dispenser system without a pump interface. The robotic system may further include a computer control system connected to flow and pressure sensors. The system may directly feed an applicator without an intervening pump.

SUMMARY OF THE INVENTION

A system applies an odor abating solution to an odor-emitting surface from a storage compartment having a solution of iodine having a concentration of at least 0.0005% by total weight of the solution of $I_2$;

a misting system having mist nozzles that are supported over the odor-emitting surface, creating an aerial environment between the odor-emitting surface and the mist nozzles;

misting nozzles configured to spray droplets of the solution into the aerial environment over the odor-emitting surface so that, in the absence of any air movement exceeding 1 kilometer/hour, at least 75% of the droplets will be suspended in the aerial environment over the odor-emitting surface for at least 10 seconds, allowing at least 1% by total weight of the $I_2$ in the solution to react with emitted odor before the 75% of the droplets are deposited on the odor-emitting surface.

The solution of iodine should be a liquid anti-odorant solution with: a) at least 80% of total weight of a carrier liquid comprising water, alcohol or a mixture of water and alcohol; and h) at least 0.001% by weight of the solution of $I_2$. There may be sufficient acid in the solution to provide a pH of less than 6.7 in the solution. The odor-emitting surface may be an open pit, a landfill, temporary waste storage site or an open environment, even where wind conditions may be a factor (by using a screen as the mist is in the air).

A method and system for abating odor in a waste transfer system environment includes an enclosed structure having a first mass of waste materials comprising a first concentration of organic materials and a first concentration of inorganic solid materials, and a separation system that creates a second mass of waste materials comprising organic materials and a third mass of waste materials comprising inorganic materials, wherein the second mass has a second concentration of organic materials that is higher than the first concentration of organic materials and the third waste mass has a second concentration of inorganic materials that is higher than the first concentration of inorganic materials. The enclosed structure having a misting system that provides a mist to an aerial environment over at least one of the first mass of waste materials and the second mass of waste materials so that the mist is dispersed in the aerial environment which comprises odorous gaseous waste emitted from at least the first mass of waste materials and second mass of waste materials. The mist comprising an anti-odorant solution comprising at least 80% by total weight of a composition of the mist as water, or water and alcohol, and a first iodine concentration in the mist of at least 0.0005% or at least 0.001% by weight iodine ($I_2$) to the total weight of mist emitted. As the mist is reacting with molecules of the odorous gaseous waste in the aerial environment, any total amount of residual iodine ($I_2$) that settles on the first waste mass and second waste mass will be less than the total amount of iodine ($I_2$) that has been emitted with the mist into the aerial environment, as some of the original iodine ($I_2$) has reacted with some of the molecules of the odorous gaseous waste within the aerial environment and has been converted to an iodo- or -iodide component of a compound.

BRIEF DESCRIPTION OF THE FIGURES

FIG. 1.1 shows a Prior Art process chart of the waste hydrotransportation system and collection unit including a wet waste lift station and a wet waste transfer station and wet waste generator collection apparatus and wet organic waste processing plant.

FIG. 1.2 shows a Prior Art process chart of the present invention including generator, wet organic waste and dry waste generator containers, a transportation and preparation vehicle or unit, and wet organic waste processing plant and dry waste processing facility.

FIG. 2 shows a top view of a Prior Art transportation and preparation vehicle or unit.

FIG. 3 shows a cross section view of a Prior Art transportation and preparation vehicle or unit.

FIG. 4 is a schematic diagram representation of a Prior Art automated material transfer station of the present invention.

FIG. 5 is a block diagram representation of several configurations of Prior Art material transfer systems useful in accordance with the present invention.

FIG. 5A is a side view of treatment of dry waste material in a system of the present technology.

FIG. 6 is a schematic of a solid waste segment in a housing and a misting system.

DETAILED DESCRIPTION OF THE INVENTION

A method and system for abating odor in a waste transfer system environment includes an enclosed structure. The enclosed structure can be a building (temporary or permanent), a tent, a truck or train carrier and the like. The enclosed structure will have moved into and through it a first mass of waste materials having a first concentration of organic materials and a first concentration of inorganic solid materials. These are the materials collected for separation into respective types of waste that are sent to various locations for disposal or separate treatment. There is also a separation system (automatic, manual or mixed manual and automatic) that creates a second mass of waste materials which has organic materials and a third mass of waste materials which has inorganic materials, wherein the second mass has a second concentration of organic materials that is higher than the first concentration of organic materials (that is there is a lower concentration of inorganic materials present) and the third waste mass has a second concentration of inorganic materials that is higher than the first concentration of inorganic materials (as some organic materials have been removed). The enclosed structure has a misting system (spray, misting or atomizing are included within the generic term of "misting" or "mist") that provides a mist to an aerial environment over at least one of the first mass of waste materials and the second mass of waste materials so that the mist is dispersed in the aerial environment which comprises odorous gaseous waste emitted from at least the first mass of waste materials and second mass of waste materials. The misting is preferably performed over both the first waste mass and the second waste mass. The mist is an anti-odorant solution comprising at least 80% by total weight of a composition of the mist as water, or water and alcohol, and a first iodine concentration in the mist of at least 0.0005% or at least 0.001% by weight iodine ($I_2$) to the total weight of mist emitted. As the mist is reacting with molecules of the odorous gaseous waste in the aerial environment, any total amount of residual iodine ($I_2$) that settles on the first waste mass and second waste mass will be less than the total amount of iodine ($I_2$) that has been emitted with the mist into the aerial environment, as some of the original iodine ($I_2$) has reacted with some of the molecules of the odorous gaseous waste within the aerial environment and has been converted to an iodo- (organically or inorganically combined iodine atom) or -iodide (inorganic or organic salt) component of a compound.

The iodine ($I_2$) solutions may be described as follows.

A liquid anti-odorant solution is provided which may contain by way of non-limiting examples:

1. A liquid anti-odorant solution with: a) at least 80% of total weight of a carrier liquid comprising water, alcohol or a mixture of water and alcohol; and b) at least 0.001% by weight of the solution of $I_2$. There is preferably sufficient acid in the solution to provide a pH of less than 6.5 or less than 6.7 for stability.

2. Another description is a solution as: a) at least 80% of total weight of a carrier liquid comprising water, alcohol or a mixture of water and alcohol; b) at least 0.0005% by weight of the solution of $I_2$ (e.g., at least 10, at least 15 or at least 20 ppm) and/or and preferably sufficient acid in the solution to provide a pH of less than 6.5 or less than 6.7.

3. A further alternative solution may contain, by way of non-limiting examples:

At least 0.0005% or at least 0.001% by weight (or at least H) ppm of the solution) of the solution of a cation (e.g., $K^+$) and an approximately equal concentration solution of $I_2$; at least 0.0005% 0.001% by weight of $CuSO_4$; and preferably sufficient acid in the solution to provide a pH of less than 6.5 or less than 6.7.

These solutions of the present invention may be provided in numerous formats.

DETAILED DESCRIPTION OF THE INVENTION

One aspect of technology described herein includes a liquid antimicrobial solution with:

A) at least 80% of total weight of a carrier liquid comprising water, alcohol or a mixture of water and alcohol;

at least 0.0005% by weight of the solution of $I_2$; (e.g., 0.0005 to 0.10% by weight, 10-100 ppm, 10-80 ppm, 10-50 ppm, 10-30 ppm iodine), and/or E and sufficient acid (even with buffering) in the solution to provide a pH of less than 7.0, preferably less than 6.5; or B) at least 80% of total weight of a carrier liquid comprising water and dissolved iodine, alcohol or a mixture of water and alcohol;

at least 0.001% by weight of the solution of ($I_2$ (e.g., 0.0005 to 0.10% by weight, 10-100 ppm, 10-80 ppm, 10-50 ppm, 10-30 ppm iodine), and/or F;) and cation (e.g., $K^+$) and residual, non-critical;

at least 0.0005% or at least 0.001% by weight of the solution of $CuSO_4$; and sufficient acid in the solution to provide a pH of less than 6.7, less than 6.5 or less than 6.3.

The solution may have acid in sufficient amount to provide an initial pH of from 2.0 to 4.8 or 3.5 to 6.0, and then be buffered to moderate the pH to a less acidic (but still acidic) level. The solution has a preferred acid of sulfamic acid and may then be buffered back to a pH of 5.8-7.0, preferably 6.0-6.5.

The solutions of the present technology may be provided, by way of non-limiting examples, wherein the acid is sufficient in an amount to provide a pH of from 5.5 to 6.7, especially where the acid comprises a sulfamic acid compound, such as a sulfamic acid compound having the formula:

$$NR_2SO_3H,$$

wherein R is independently selected from the group consisting of hydrogen and electron-withdrawing groups, or a sulfamic acid compound having the formula:

$$NR_2SO_3H,$$

wherein R is independently selected from the group consisting of hydrogen, halogen, cyano, C1-C6 alkyl, C1 to C6 substituted alkyl, perhalo alkyl, halosubstituted alkyl, and electron-withdrawing groups.

One embodiment may have least one R as hydrogen, or exactly one R as hydrogen. A spherical encapsulation system optionally and additionally may be provided (in addition to the spray) as a core of liquid comprising the solution of the present technology having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight. For example, the encapsulation system may have the core as a droplet of the solution having a diameter of from 0.0001 to 1 mm. The encapsulation system may have the droplet of solution comprises 10-90% average percentage by weight of the encapsulation system.

Another encapsulation system comprising droplet cores of aqueous liquids comprising the solution of the present technology having diameters of from 0.0001 to 0.5 mm of aqueous liquid having a surface, said droplets having a stabilizing layer comprising hydrophobic particles with a volume weighted mean particle diameter of from 0.05 to 25 micrometer hydrophobic particles on said surface, said stabilizing layers being generally spherical, with at least 25% by number of all droplets encapsulated by hydrophobic particles in said encapsulated system having less than a 25% deviation in diameter in cross-sections. The layer of hydrophobic particles may be a layer of particles with less than 80% by number of said particles being bonded to any adjacent particle.

One additional subgeneric format includes a microencapsulated particles comprising a frangible shell having a liquid core of the solution of the present technology. The frangible shell may be a polymer and the microencapsulated particles have a number average diameter of 0.001 to 2 mm (or larger, such as up to 5 mm).

Another additional subgeneric format includes an iodine delivery system comprising a hydrocolloid entraining at least 20 by weight of the delivery system of the solution of the present technology.

Still another iodine delivery system includes a clay entraining at least 20 by weight of the delivery system of the solution of the present technology or an iodine delivery system comprising a flexible polymer having droplets of the solution of the technology disclosed herein dispersed therein. This last iodine delivery system may have the droplets with a number average diameter of 0.001 to 2 mm. Stable Iodine Liquid Compositions/Solutions (Ready to Use and Concentrate)

An iodine solution is acidified by the addition of an acid that (alone) produces a pH of less than 6.7 at 1.0 N in deionized water and preferably less than 6.5 under those parameters. Typical acids may be organic acids, inorganic acids, Lewis acids, HCl, HI, HBr (halogenic acids), $HNO_3$, $HClO_4$, $H_2SO_4$, $H_2SO_3$, and especially the family of sulfamic acids.

The iodine environment can be provided in numerous and varied tasks and services and even in combination with other additives such as stable active solutions or film-breaking compositions such as acids (e.g., sulfamic acid, hydrochloric acid, sulfuric acid, enzymes, etc.). At present, the most widely known and accepted acidizing agents include HCl, sulfamic acid, lactic acid, citric acid, and acetic acid, all with varying degrees of reactivity for descaling. The effect of acidizing with iodine gas in solution, however, also attends with additive anti-odorant effects, and when the acidized iodine is combined with sulfamic acid, a powerful and effective method is provided for dissolving and remediating biofilms, and chelating heavy metals which may be solubilized by the process, or otherwise contained in water, especially after physical disruption as described herein.

Sulfamic acid is also a primitive surfactant, and when added to free iodine in water and stabilized by varying added compounds such as silicates (e.g., sodium metasilicate) and phosphates and sulfonates (e.g., sodium xylene sulfonate or phosphate), yields a disinfecting and biofilm removing detergent compound which is active within the technologies described herein for oilfield or watershed applications as a single formulary product. The term a "sulfamic acid compound" or a member of the family of sulfamic acids or class of sulfamic acids is herein defined as any sulfamic acid central moiety with a single substituent on the amide group of the sulfamic acid moiety or sulfamic acid core structure that still allows the sulfamic acid derivative in the family of sulfamic acids to display a pH of less than 6.8 at 0.5N in deionized water, preferably less than 6.5 under those parameters 5.5 to 6.7, 5.5 to 6.2, and 4.0-6.7, and 3.0 to 6.7 and even lower levels of acidity up to 6.5, up to 6.6 or up to 6.7 pH). As non-limiting examples of these known sulfamic acid family compounds are sulfamic acid, iodosulfamic acid, chlorosulfamic acid, bromosulfamic acid, fluorosulfamic acid, alkylsulfamic acid (with C1-C8 carbon groups, whether linear, branched or cyclic, such as cycloheylsulfamic acid, and substituted or not, such as trifluromethylsulfamic acid, pentachloroethylsulfamic acid, etc.), cyanosulfamic acid, any electron-withdrawing group on the amide position of the sulfamic acid and even lightly electron-donating groups that do not change the sulfamic acid from an acid to a base at 1.0N in deionized water.

The formula for sulfamic acid is $NH_2SO_3H$ and the corresponding formula for a sulfamic acid compound is represented by:

$NR_2SO_3H$, wherein R is independently selected from the groups described above, such as hydrogen, halogen, cyano, C1-C6 alkyl or substituted alkyl, perhalo alkyl, halosubstituted alkyl, electron-withdrawing groups, mild electron-donating groups and the like. It is preferred that at least one R group is hydrogen.

The sulfamic acid is both an acidifying agent (and other acids may be used) and a primitive surfactant. CupriDyne™ anti-odorant compositions in water is stabilized (free iodine is continuously available) by lowering pH to 5.5-6.7. Even the CuI resulting component is held in solution. The addition of surfactants, such as sodium metasilicate and sodium tripolyphosphate assists in completing a detergent preparation formula. The solutions may have normal levels of iodine therein (e.g., at least 5 ppm or may be concentrated for dilution with greater than 50 ppm, greater than 100 ppm, greater than 200 ppm, up to solubility limits of iodine in aqueous or alcohol solvents.

It has also been found that the order of mixing certain combinations of ingredients simplifies the dissolution of individual ingredients and improves some final solutions properties (such as transparency). For example, it has been found that first dissolving the buffering agent or the acid, and then dissolving the acid or buffeting agent, respectively, makes it easier to dissolve the active components and make it easier to provide a transparent active iodine solution. The two iodine-forming reactive ingredients may then be added into the acid-buffer solution. The $CuSO_4$ may be first dissolved into the acid-buffer solution and then the alkali or alkaline iodide is dissolved in the acid-buffer/$CuSO_4$ solution. The iodide may be added as Li, Na, K, Ca, Mg, $NH_4$ iodide or the like. In certain medical and environmental uses, the selection of the particular cation may be more than merely a matter of convenience or choice of equivalents. The particular cation may be desirable as Na in certain medical applications where Li or K is less desirable. The various cations may be selected for design and concentration to maintain an appropriate isotonic balance with patients and their cells and vessels. The concentration of the cations and anions and iodine in solution, the pH and the selection of particular incidental cations and anions are selected to achieve balances of properties in the solutions.

The solutions of the present technology may be added to, combined with and/or modified to replicate other known medical solutions, as with the case of "Normal" saline, where 0.9% w/w NaCl in sterile water is involved, so that it is possible to compute the Na content to include a change from KI to NaI in this technology. This can be used to create a solution with 260 to 310 mOsm/L osmolality, or preferably between 275 and 300 mOsm/L osmolality, and approach balance with the normal Na or cation pressure in tissue. In one preferred embodiment, sodium iodide replaces portions of (5%, 10%, 20%, 30%, 50%, 60%, 75%, 80%, 90%, 95%) or all of the potassium iodide.

On another level, a lactated Ringer's solution is possible. One liter of lactated Ringer's solution ordinarily contains:

130 mEq (80-200) of sodium ion=130 mmol/L
109 mEq (70-180) of chloride ion=109 mmol/L
28 mEq (15-50) of lactate=28 mmol/L
4 mEq (2-8) of potassium ion=4 mmol/L
3 mEq (1.5-4) of calcium ion=1.5 mmol/L"

An equivalent or partial replacement equivalent or mixture with solutions according to the present technology may also be prepared. The sodium, chloride, potassium, calcium and chloride in the standard lactated Ringer's solution may vary among each other by percentages n the order of (5%, 10%, 20%, 30%, 50%, 60%, 75%, 80%, 90%, and 95%) among each other. Tincture of iodine may also be used. Tincture of iodine or iodine tincture is an antiseptic, it is also called weak iodine solution. It is usually 2-7% elemental iodine, along with potassium iodide or sodium iodide, dissolved in a mixture of ethanol and water. Tincture solutions are characterized by the presence of alcohol.

These stable solutions are advantageously deliverable in many different forms, besides direct liquid delivery as a wipe, spray or brush application. For example, the solutions may be provided as a spherical encapsulation system comprising a core of liquid comprising the solution of the present technology having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight. The core may, for example, comprise a droplet of the solution having a diameter of from 0.0001 to 1 mm. The encapsulation system may have the droplet of solution comprises 1.0-90% average percentage by weight of the encapsulation system. These solutions may be directly applied, sprayed, imbibed in a fabric carrier and applied as a wipe, or gelled and the like.

One skilled in the arts related to this technology, including antiseptic and antimicrobial fields, polymer chemistry, emulsion chemistry and encapsulation technology can provide specific alternatives and equivalents within the scope of the generic disclosure and enablement disclosed herein.

Each reference cited in this disclosure are incorporated by reference in their entirety. Terms must be read with their broadest common meaning unless specifically limited. For example, where a "nozzle" is stated or recited, that term means any outlet port (even a hole in a pipe) where liquid is emitted as droplets. This encompasses holes, fixed size nozzles, adjustable nozzles, plug-in spouts, spouts, and the like.

When spraying the droplets with iodine therein, some minimal caution must be used by workers in the area. As with most materials and elements, there is a level at which breathing in immediate large concentrations over a long period can be hazardous. For iodine that may be about 0.000001 ppm in air. As the droplets can have low level of iodine, and as the droplets are dispersed in air, these recommended concentrations in a closed environment can be avoided. Also, because the droplets are easily captured by filters, workers can use commercial face masks that are water adsorbent or water absorbent for adequate protection.

The misting systems which can be used in the practice of the present technology include Prior Art systems that are commercially available. For purposes of enablement, but without limiting the practice of the present invention to these misting systems, the following disclosure and Figures are presented.

FIG. 1.1 shows Prior art (Published US Patent Application Document 20030003568 (Yilmaz)) hydrotransportation of waste collection and processing system 10 including a waste generator 11, preferred wet waste generator collection apparatus 12 and waste hydrotransportation system 17. Waste commonly called municipal or solid waste is transported using system 17. Said hydrotransportation system 17 includes a collection unit consisting of one or a combination of collection apparatus 12 and wet waste lift station 17.1 and wet waste transfer station 17.2, and a transportation pipe/main 17.3. Said collection unit is designed to add water and reduce said wet waste in size for hydrotransportation using one or a combination of a generator grinder and generator cutter. Collection apparatus 12 is preferred to add water and reduce said wet waste in size for hydrotransportation using one or a combination of a generator grinder 12.1 and generator cutter 12.2.A. A wet waste processing plant 20 receives wet waste from one or a combination of wet waste lift station 17.1 and wet waste transfer station 17.2 and wet waste transportation vehicle/unit 16. Wet waste is prepared by one or a combination of wet waste generator collection apparatus 12 and wet waste lift station 17.1 and wet waste transfer station 17.2 and wet waste transportation vehicle/unit 16 for hydrotransportation system 17. Wet waste 19 is processed using wet waste plant 20 which uses one or a combination of aerobic and anaerobic methods for storage 80 and reuse 81. Any waste which cannot be cost effectively processed for reuse is stored or deposited in a small landfill or bioreactor 82.

FIG. 1.2 shows interconnected waste collection and transportation and processing system 10 including summary of the present invention showing a waste generator 11, preferred waste collection apparatus and sub-system including wet organic waste generator container 19 and dry waste generator container 18 for separation of waste into groups of at least wet organic waste 19 and dry waste 18 as initially contained in a wet organic waste generator container 12 and a dry waste generator containers 13 respectively, a transportation and preparation vehicle/unit and sub-system 16, wet organic waste processing plant 20, and dry waste processing facility 40. Wet organic waste generator container 12 includes a cover 12.1 and at least one wheel 12.2 and handle 12.4 and a biodegradable removable liner 12.3 which covers the inside wall of said wet organic waste generator container 12. Dry waste generator container 13 includes a cover 13.1 and handle 13.5 and at least one wheel 13.2 and removable liner 13.3 which covers the inside wall of said dry waste generator container 13 and an adjustable partitioning system 13.4 for different groups of dry waste portion of the waste. Said transportation and preparation unit 16 is preferred to have two transportation containers 14 and 15 for wet organic waste 19 and dry waste 18 respectively for the purpose of preparation and initial processing. Wet organic waste 19 is prepared through processing plant 20 for reuse 81 and storage 80. Dry waste 18 is prepared through processing 40 for storage 80 and reuse 81. Any waste which cannot be cost effectively processed for reuse is stored or deposited in a small landfill or bioreactor 82.

FIG. 2 and FIG. 3 shows a top view and a cross section of a transportation and preparation vehicle/unit and sub-system 16 which includes wet organic waste and dry waste transportation vehicles or units that have containers 14 and 15 respectively. Wet organic waste transportation container 14 and dry waste transportation containers 15 receive waste from wet organic waste generator container 12 and dry waste generator container 13 respectively. Preparation and initial processing of wet organic waste 19 is primarily achieved during collection and transportation as follows. Wet organic waste 19 is accepted through feeder 14.1 and prepared by transportation grinder 14.2 while being watered by water spray nozzle 14.3 which is connected to water tank 14.4. Transportation watering unit 14.3 is turned on and positioned as needed. Said waste 19 is contained in 14.5 which can also be used to separate grease and discharged using 14.6 and valve 14.7.

Preparation and initial processing of dry waste 18 is primarily achieved using wet organic sub-system and dry waste sub-system during collection and transportation as follows. Dry waste 18 is separated as much as possible using generator container 13 and dry waste transportation container 15. Dry waste transportation container 15 consist of one section 15.1 or multiple sections 15.5, 15.6, 15.7, 15.8 using adjustable partitions 15.2, 15.3, and 15.4 respectively for the purpose of segregating dry waste as a function of waste stream and transporting said waste for processing 40. Although preferred to be segregated where cost effective, dry waste 18 can be collected and transported without segregation as a combined dry waste using 15.1. Dry waste processing 40 would segregate said combined dry waste for reuse using 15.1 for transportation and 40 for processing. Local conditions and characteristics of the waste stream would be one of the primary selection criteria for above mentioned options of combined or segregated dry waste collection and transportation.

Figure 4:
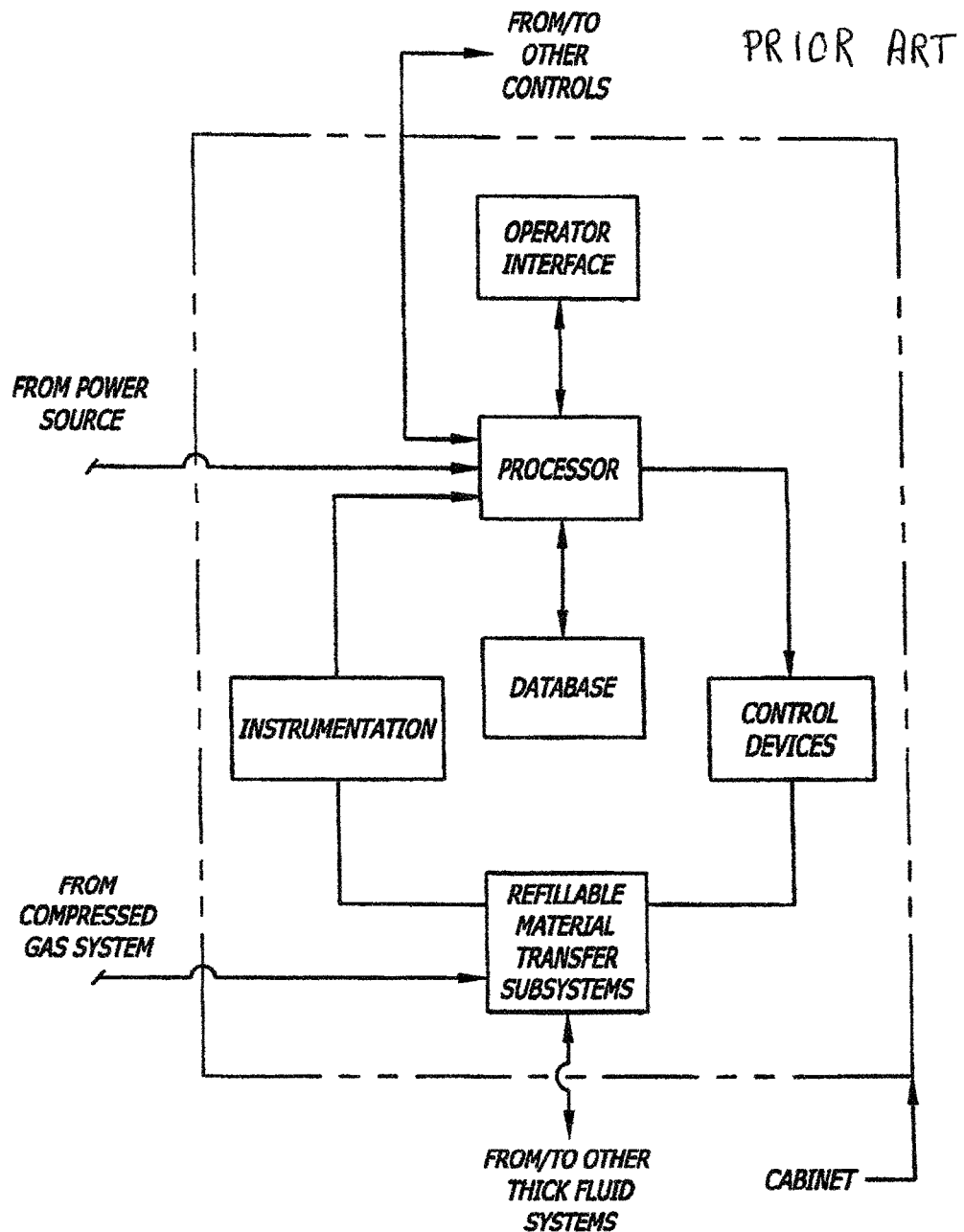

Referring now to FIG. 4 (Prior art disclosed in US Patent Application Document 20140166693, Williams), one or more automated, refillable material transfer subsystems 110 of the present invention may be housed within a "cabinet" so as to provide a comprehensive automated material transfer station 1000. The automated station may be configured into a plurality of partitions including a control section 1010 and a material transfer section 1020. The automated material transfer station includes a housing having a cover 1030 and a floor and or skid-type configuration 1040. The material transfer station includes outer walls 1035, and may include one or more doors windows and other access ways, as appropriate. The automated transfer station is configured to be "plug and play," and may be moveable about an industrial manufacturing site, storage area, loaded onto the back of trucks, trailers or railcars, and otherwise moveable from place-to-place. Depending on the size of the containers and internal control component, the automated material transfer station may be a few feet tall and wide or configured with significantly larger dimensions. Accordingly, the automated station may be configured to be stationary within a warehouse, a factory and other working environments, or the automated station may be configured to be movable or portable from one desired location to another.

In the control section 1010 of the automated material transfer station 1000, it is contemplated that the control section will be divided into several compartments 1060, 1070 with shelving or other partitions 1065, 1075. Similarly, the material transfer section may be configured with a single compartment 1050, or may be divided into sub-compartments as appropriate. It is expected that a heating, ventilating and air conditioning (HVAC) system will be supplied to the automated material transfer station such that the control section may be cooled, heated or otherwise air-conditioned separately from the material transfer section. An insulated dividing wall 1080 may be constructed between the two sections so as to isolate the two temperature sections. Not shown in FIG. 4 are the heating, ventilating and air-conditioning ducts, compressors and other components. Such devices may be self-contained within the material transfer station or again "plug and play" to the HVAC system where the control station is positioned.

Referring to the control section 1010 of the automated material transfer station 1000, a first compartment 1060 may be configured to house a microprocessor 310 and multiple programmer logic controllers (PLCs) 512, 522, 532 and 552. These PLCs may be electronically or otherwise connected to the microprocessor via a control conduit 1310 or other suitable hard-wired or wireless connections. The PLCs may be connected by multiple conduits, cabling, wireless connections 1330 to the instrumentation and other devices associated with the material transfer subsystems. The microprocessor may further be configured to connect via a cabling conduit or wireless connection 1320 to a cabling tray or other conduit system 1090 so as to connect the microprocessor to a display system 320 and input output system 340, a printing system 370 and modem 350 having connections 1325 to the conduit system.

Further, the microprocessor 310 may be connected to an analog-to-digital (A/D) and/or digital-to-analog system 360. The A/D system may be connected to an outside conduit 1120 for receipt of signals from material transfer devices in same station, other stations or external devices such as pumps, spray devices and robots. The automated control station may further include a communication connection 1110 for connecting to the computer modem, to a phone line, data signals and wireless signals. The automated station may further include switches, controls and other operator interface devices 1130 located on the outside of the cabinet. The automated station also includes a power coupling 1150 for supplying AC and/or DC power. The automated station may also include its own power generating station and uninterruptible power supply.

The material transfer section 1020 of the automated material transfer station 1000 includes one or more refillable (intelligent, automated) material transfer subsystems 110 having vessels 120, lid lifting mechanisms 130, main bodies 150, fluid manifolds 140 and gas inlets 160. Although not fully described regarding this embodiment, the other features of the refillable material transfer systems described herein and incorporated by reference are applicable to this embodiment. The automated material transfer station may include outside couplings for gas inlet and outlet 1210, fluid inlet 1220, fluid outlet 1230 and other connections as appropriate. Instrumentation, such as pressure and temperature sensors, may be connected directly to the control system section or may be connected to an outside coupling 1125. Such a coupling may allow input and output data from other automated stations and remote devices within a manufacturing plant or other facility, for example, control systems for pumps, spray devices and robotics. Similarly, instrumentation signals coming from the material transfer section 1020 through the outside electric connection 1125 may be connected directly into the input electrical connection 1120 to the A/D device 360, which in turn may connect to the microprocessor 310 and logic controllers 512-552. Instrumentation and control devices located within the material transfer section 1020 and vessel compartment 1050 may be connected directly to the outputs from the logic controllers via cabling 1330 or other suitable systems, such as wireless connections (for example, radio frequency and microwave signals).

Figure 5:
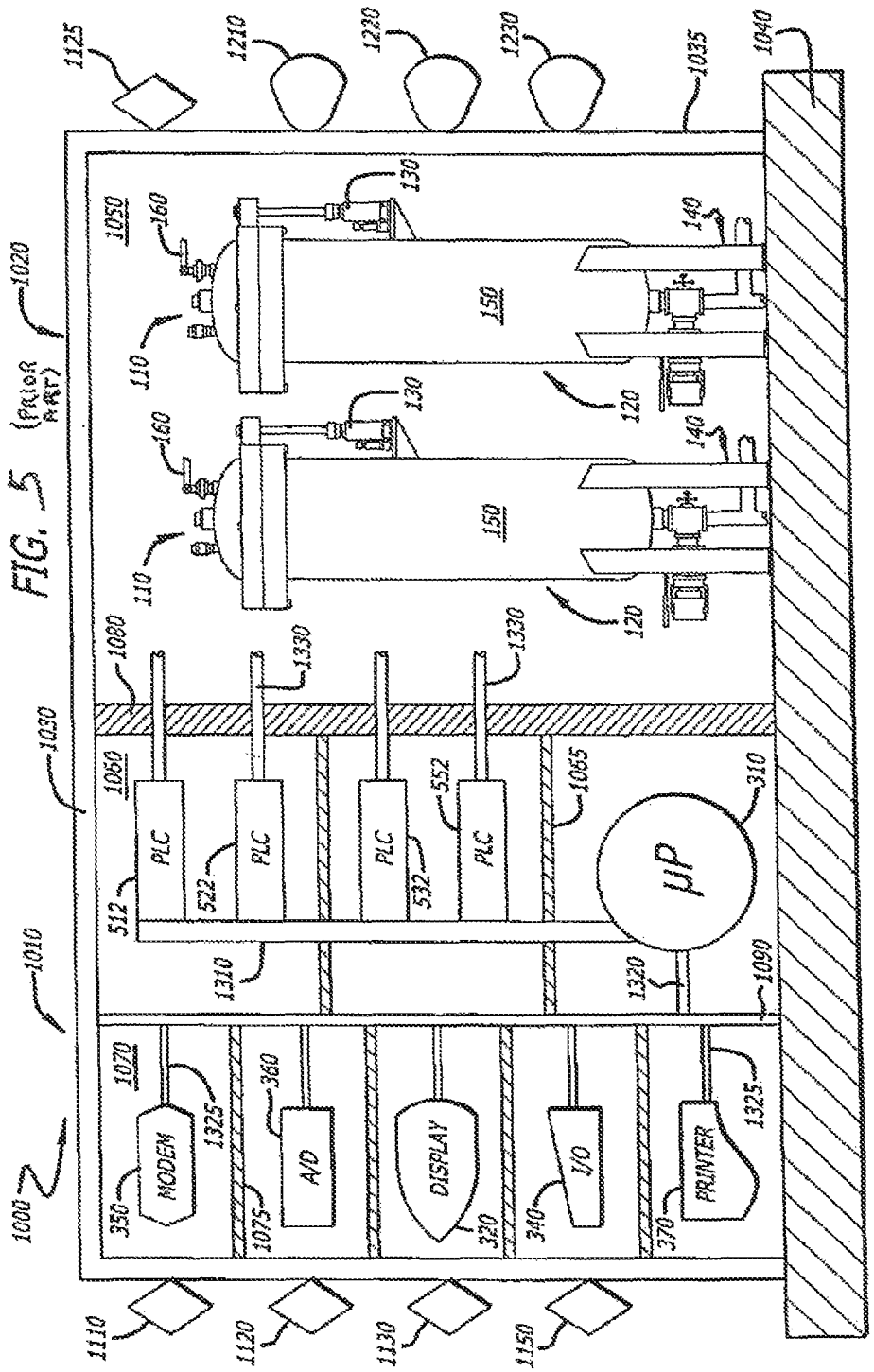

When at least one material transfer subsystem 110 is included in the material transfer section 1020 of the automated material transfer station 1000, the material vessels 120 may be configured such that one system is filling as another system is emptying. The vessels may be the same size or of different sizes (FIG. 5, as disclosed in US Patent Application Document 20140166693, Williams). In addition, compound material transfer subsystems may be configured such that two or more vessels of different sizes may be connected in series to obtain efficiencies as a first larger vessel (having a force transfer device of a first aspect ratio) feeds one or more second smaller vessels that may have force transfer devices with different aspect ratios than the larger vessel. The material transfer subsystems may feed pumps and/or directly feed material to a device such as a robotic sprayer (applicator) or "shot meter." Likewise, multiple vessels may be in fluid communication with one or more material (fluid) manifolds that are connected to one or more pumps and applicators. As shown in FIG. 5, the automated material transfer system may be externally fed by larger material transfer systems, such as those on the back of a railcar or truck. Further, the vessels may be positioned side by side or stacked on top of each other for efficiency of storage within the compartment 1050 of the material transfer section 1020 of the automated material transfer station 1000. Large storage tanks of fluid and other materials may be configured to feed several such automated control stations.

The vessel (container) 20, 120, force transfer device 90, and/or other items in contact with the material may be equipped with a lining (not shown). The materials of construction suitable for the lining may include, but are not limited to, alloys, composites, elastomers, metals, plastics, polymers, rubbers, wood fiber and other natural and synthetic materials. The forms of the lining may include, but are not limited to, attached (form-fitted) and independent (stand-alone); flexible and rigid; and applied and pre-formed.

FIG. 5A is a side view 400 of treatment of dry waste material 406 in a system of the present technology. The misting system 410 is shown with its liquid conduit 412 to a source of the iodine liquid solution (not shown). An aerial environment 402 is shown between the misting system (e.g., nozzle or port) 410 and the surface 408 of the dry waste material 406. When the liquid iodine solution is misted by the misting system 410, droplets 404 are misted into the aerial environment 402 where odorous compounds are abated by iodine in the droplets 404, at least for a ten second period.

Of the available technology, misting—with either water or odor-reducing products—is still the industry's method of choice, both inside buildings and outside, around green-waste operations and for perimeter spraying.

Odor control agents range from products that mask malodors with something designed to smell pleasanter to new generations of neutralizers that, although widely used in other municipal applications such as wastewater treatment plants, have yet to catch on the solid waste industry.

80% of odors humans find offensive are the result of nitrogen- or sulfur-bearing compounds. Until material containing these compounds starts to decompose, people are unaware they're around, usually in combination with carbon and oxygen atoms. But when decay occurs, the nitrogen and sulfur atoms are rearranged into smaller molecules that give off odor when they're volatilized as gases into the air. The challenge for controlling odor is that, in some cases, relatively few molecules—as little as one part per billion—need be present for sensitive noses to notice. Masking malodors with a product designed to smell better is a traditional approach. Two others are oxidation, which inhibits the reaction that generates odor, and encapsulating agents.

Masking agents merely add more odor. Transfer station operators who find pleasant odors too long ingested to be as unpleasant as the malodors they're designed to substitute are experimenting with other chemical options. Rainbow Disposal in Huntington Beach, Calif. uses a product called BioMagic, which works through oxidation using dissolved oxygen. RMB Engineering is marketing Odor X, which the company describes as an odor neutralizing agent ("a water-based mix of plant oils and surfactants") with Triad Industries's dry vapor dispersal system. When the Odor X vapor is mixed with the air, the odors that pass through the air current are emulsified and carried off. Carrying off odors does not eliminate the odors from the environment.

Here we are listing the top 3 most common emissions from waste materials.

Hydrogen Sulfide—As the waste decomposes in the stream, oxygen is used up. This state causes the sulfate ions that are present in human, animal, and biological waste and most sources of water, to break down into $H_2S$ gas and $H_2O$.

Ammonia—Resulting from the breakdown of compounds in the solid and liquids of the sewage stream and a high pH level, the ammonia ion and ammonia gas is formed and fluctuates at different parts of the waste treatment process.

Methane—A dual edged sword, methane gas has the distinction of not only being harmful to humans and animals at low levels, but is also flammable. Methane is formed when plant or animal matter decays. There are many other gas emissions from raw sewage as it progresses through it's breakdown process. Also formed are volatile organic compounds VOCs, pathogens, and bacteria.

Figure 6:
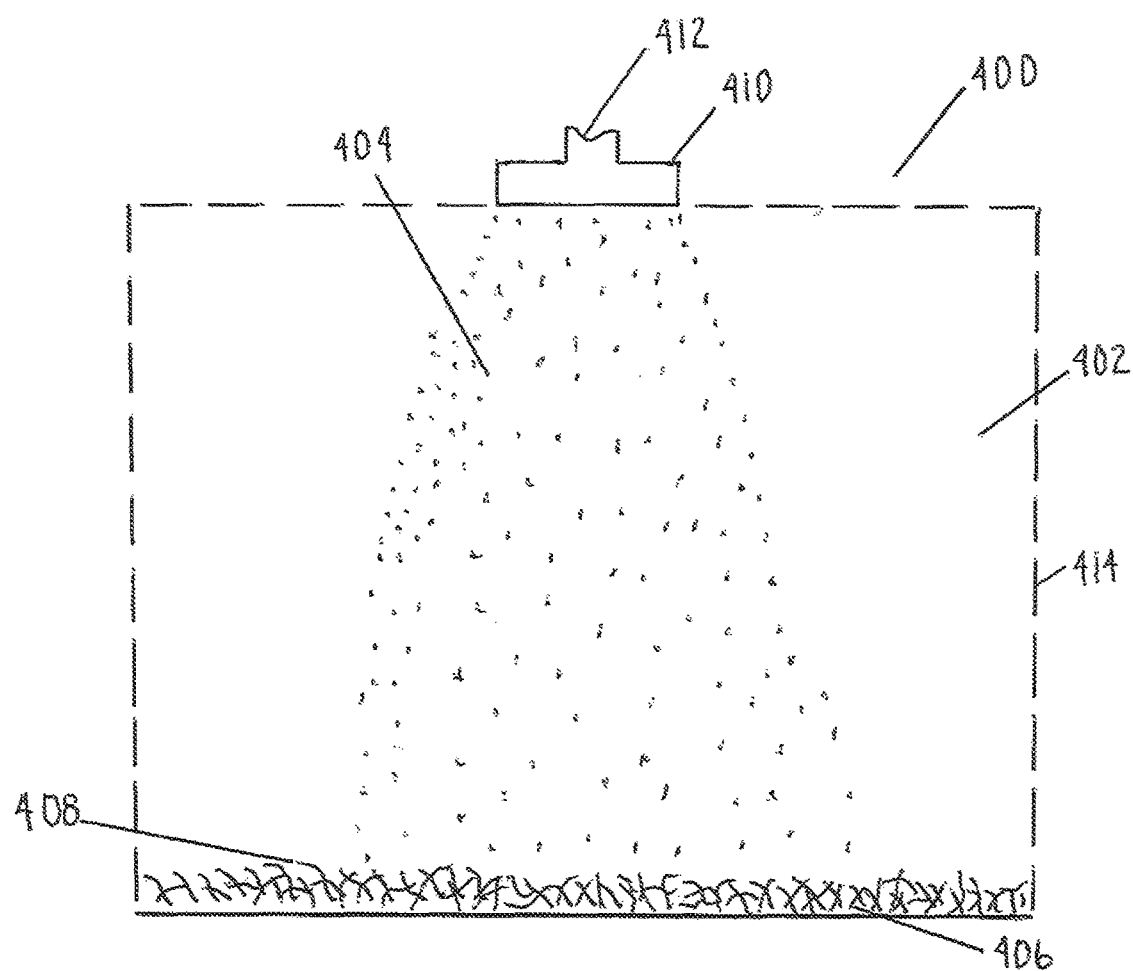

FIG. 6 is a schematic of a solid waste segment 406 in a housing 414 and a misting system 410. The housing 414 contains an aerial environment 402 over the top surface 408 of the separated solid waste segment 406. The misting system 410 is connected to a source 410 of odor abating liquid (not shown), and the misting system 410 emits mist 404 into the aerial environment 402 some mist 404 contacting the top 408 of the separated solids waste segment 406 after being within the aerial environment 402.

What is claimed:

1. A method of abating odors emitted from an odor-emitting dry waste surface within a waste management facility comprising:

providing a first mass of waste, separating the first mass of waste into an odor emitting wet waste mass and an odor emitting dry waste portion;

storing the dry waste portion within the waste management facility, and then a) providing a container of liquid iodine solution having a concentration of at least 0.0005% by weight iodine to the total weight of liquid iodine solution;

b) providing a misting system in fluid communication with the container over the odor-emitting dry waste surface to create an aerial environment over at least the odor-emitting dry waste surface and below the misting system;

c) misting the liquid iodine solution into the aerial environment to create droplets over at least the odor-emitting dry waste surface from nozzles; and d) moving the nozzles relative to the odor-emitting dry waste surface, thereby providing mist of the liquid iodine solution into the aerial environment having odorous gases emitted from the odor-emitting dry waste surface so that iodine in the solution reacts with odorous gases and abates odor within the aerial environment, wherein misting is performed so that, in the absence of any air movement exceeding 1 kilometer/hour, at least 75% of the droplets will be suspended in the aerial environment over at least the odor-emitting dry waste portion for at least 10 seconds before droplets from the at least 75% droplets are deposited on the odor-emitting surface.

2. The method of claim 1 wherein the odor-emitting surface comprises both odor emitting wet waste mass and the odor emitting dry waste portion of waste material within a waste transfer station.

3. The method of claim 2 wherein a storage compartment storing the liquid solution of iodine as an odor-abating liquid which is pumped or gravity fed from the container into the misting system, and the waste management facility is automated, with a microprocessor controlling feed of the liquid iodine solution to the nozzles.

4. The method of claim 3 wherein the solution of iodine comprises a liquid anti-odorant solution with: a) at least 80% of total weight of a carrier liquid comprising water, alcohol or a mixture of water and alcohol; and b) at least 0.001% by weight of the solution of iodine.

5. The method of claim 4 wherein there is sufficient acid in the solution to provide a pH of less than 6.7 in the solution.

6. The method of claim 1 wherein the odor-emitting surface comprises a portion of waste matter in a landfill.

7. The system of claim 2 wherein a portion of the waste matter over which the solution is misted comprises that portion of waste matter within the waste transfer system having a highest concentration of organic matter as compared to any other portion in the waste transfer system.

8. The system of claim 4 wherein the anti-odorant is free of added fragrances.

9. A method of abating odors emitted from an odor-emitting dry waste surface within a waste management facility comprising:
   providing a first mass of waste,
   separating the first mass of waste into an odor emitting wet waste mass and an odor emitting dry waste portion;
   storing the dry waste portion within the waste management facility, and then
   a) providing a container of liquid iodine solution having a concentration of at least 0.0005% by weight iodine to the total weight of liquid iodine solution;
   b) providing a misting system in fluid communication with the container over the odor-emitting dry waste surface to create an aerial environment over at least the odor-emitting dry waste surface and below the misting system;
   c) providing misting solution of the liquid iodine solution into the aerial environment from outlet ports where liquid is emitted as droplets of the liquid iodine solution so that, in the absence of any air movement exceeding 1 kilometer/hour over the odor emitting dry waste portion, at least 75% of the droplets of the liquid iodine solution will be suspended in the aerial environment over at least the odor-emitting dry waste potion for at least 10 seconds; and
   d) moving the outlet ports relative to the odor-emitting surface, thereby providing mist of the liquid iodine solution into the aerial environment having odorous gases emitted from the odor-emitting dry waste surface so that iodine in the solution reacts with the odorous gases comprising at least one of nitrogen-bearing compounds and sulfur-bearing compounds and abates odor within the aerial environment.

10. The method of claim 9 wherein the odor-emitting surface comprises both odor emitting wet waste mass and the odor emitting dry waste portion of waste material within a waste transfer station.

11. The method of claim 10 wherein a storage compartment storing the liquid solution of iodine as an odor-abating liquid is pumped or gravity fed from the container into the misting system and the waste management system is automated, with a microprocessor controlling feed of the liquid iodine solution to the nozzles.

12. The method of claim 11 wherein the solution of iodine comprises a liquid anti-odorant solution with: a) at least 80% of total weight of a earner liquid comprising water, alcohol or a mixture of water and alcohol; and b) at least 0.001% by weight of the solution of iodine.

13. The method of claim 12 wherein there is sufficient acid in the solution to provide a pH of less than 67 in the solution.

14. The method of claim 9 wherein the odor-emitting surface comprises a portion of waste matter in a landfill.

* * * * *